United States Patent [19]
Pelerin

[11] 4,353,694
[45] Oct. 12, 1982

[54] DENTAL KIT FOR PERFORMING ROOT CANALS

[76] Inventor: Joseph J. Pelerin, 2756 Shallowbrook, Bloomfield Hills, Mich. 48013

[21] Appl. No.: 115,346

[22] Filed: Jan. 25, 1980

[51] Int. Cl.³ .......................... A61C 3/00; B65D 1/36
[52] U.S. Cl. ..................... 433/77; 206/369; 206/370; 206/561; 206/564; 206/63.5; 222/130; 433/102
[58] Field of Search ............ 206/370, 369, 45.19, 206/210, 561, 564, 63.5, 368; 433/77, 79, 97, 102; 222/130, 131; 312/209; 137/574, 264, 572; 220/20, 22, 23; D7/16; D24/31

[56] References Cited

U.S. PATENT DOCUMENTS

| D. 146,697 | 4/1947 | Bates | D24/31 X |
|---|---|---|---|
| D. 170,651 | 10/1953 | Palezewski | 206/370 X |
| D. 202,618 | 10/1965 | Maurer et al. | 433/79 X |
| D. 226,266 | 2/1973 | Rem | D24/31 |
| D. 240,537 | 7/1976 | Sronce | D24/31 X |
| D. 246,289 | 11/1977 | Boucher | D7/16 X |
| D. 246,561 | 12/1977 | Stahel | D7/16 X |
| 1,159,213 | 11/1915 | Grimm | 137/572 X |
| 1,186,329 | 6/1916 | Owen | 206/210 |
| 1,644,830 | 10/1927 | Henderson | 206/370 |
| 1,973,222 | 9/1934 | Moore | 206/369 |
| 2,752,970 | 7/1956 | Tapper | D7/16 X |
| 2,813,537 | 11/1957 | Lind | 222/130 X |
| 2,870,932 | 1/1959 | Davis | 220/23 |
| 3,358,826 | 12/1967 | Siegel | 206/63.5 |
| 3,451,133 | 6/1969 | Hathaway et al. | 433/77 |
| 3,460,899 | 8/1969 | Miller | 312/209 X |
| 3,532,221 | 10/1970 | Kaluhiokalani et al. | 206/564 X |
| 3,583,609 | 6/1971 | Oppenheimer | 206/369 X |
| 3,643,812 | 2/1972 | Mander et al. | 206/564 X |
| 3,697,223 | 10/1972 | Kovalcik et al. | 206/370 |
| 3,938,253 | 2/1976 | Barnard et al. | 433/77 X |
| 4,182,040 | 1/1980 | Bechtold, Jr. | 433/77 |
| 4,184,251 | 1/1980 | Kuboki | 433/77 X |
| 4,255,457 | 3/1981 | Behrins | 433/77 |
| 4,293,074 | 10/1981 | Dunsky | 206/369 X |

OTHER PUBLICATIONS

Advertisement for Tray Cart by Atdec, Box III, Newberg, Oregon, 97132, revised 9/67, 1 page.

Primary Examiner—Allan N. Shoap
Attorney, Agent, or Firm—Gifford, VanOphem, Sheridan & Sprinkle

[57] ABSTRACT

A novel dental kit is provided which contains all of the necessary implements, instruments, medicaments and supplies for performing root canal therapy. The kit comprises a housing having a pair of spaced rails for supporting a plurality of hand held dental instruments in an openly accessible position. In addition, a plurality of holder assemblies are mounted to the housing and each holder assembly contains a single type of tooth working implements and maintains them in an openly accessible position. Preferably two reservoirs are formed in the housing, one for holding a sterile liquid, such as alcohol and the other for holding an irrigatory fluid. A pump is also mounted to the housing for pumping the sterile fluid to either an accessory or a main well.

9 Claims, 4 Drawing Figures

DENTAL KIT FOR PERFORMING ROOT CANALS

BACKGROUND OF THE INVENTION

I. Field of the Invention

The present invention relates generally to medical kits and, more particularly, to a dental kit containing the tools, medicines and supplies necessary for performing root canal therapy.

II. Description of the Prior Art

In root canal therapy, the nerve canals of the tooth are removed, sterilized and subsequently filled with an inert sealer in order to prevent the future infections of the tooth nerve roots. In order to accomplish this, it is essential that the entire root canal including the root tip, be cleaned and filled to eliminate all organic matter contained within the root canal.

The usual procedure in root canals is to open the tooth into the pulp chamber and then to work down to the root end. In order to gain access to the pulp chamber, a hole is drilled through the tooth and subsequently widened by a broach. When the tooth hole to the pulp chamber is sufficiently wide, reamers are used to clean out the tooth root.

When the tooth root canal debris is removed, it is important throughout the complete root canal operation that the various implements used to clean out the root do not penetrate beyond the end of the root and irritate the periodontal tissues. The length of the root is initially ascertained by the use of X-rays. Once the length of the root is determined, a rubber stopper is placed over each reamer so that the distance between the tip of the reamer and the stopper equals the distance between the top of the tooth and the bottom of the root. Since a plurality of reamers are used throughout the root canal operation, it has been the previous practice to individually measure and position the stoppers on the various reamers. The individual measurement and placement of the stoppers on the reamers is very time consuming.

Root canal therapy, by its very nature, requires a plurality of specialized hand held instruments, implements for working on the tooth, and medicines which are otherwise unused in dental work. Heretofore, it has been the practice for dentists to individually purchase the various instruments, medicines and supplies necessary to perform a root canal operation and to assemble these instruments and supplies on a dental tray when the root canal therapy is to be performed. Such a process, however, is disadvantageous not only in that it is time consuming but also since the dentist often times neglects to arrange a certain supply or tool on the dental tray necessary to perform the particular root canal operation. Consequently, when the omitted tool or supply is required, the dentist must interrupt the root canal operation in order to obtain the necessary tool or supply. Such interruption during the root canal operation is not only time consuming but is unprofessional in appearance.

Many dentists, furthermore, perform root canal operations in different examining rooms. Thus, it is necessary to either purchase all of the instruments and supplies for performing root canal therapy for each examining room, which is very expensive, or to carry the instruments and supplies from examining room to examining room as required, which is time consuming and generally inefficient.

SUMMARY OF THE PRESENT INVENTION

The present invention overcomes the above-mentioned disadvantages by providing a dental kit having all the instruments, supplies and medicines necessary to perform root canal therapy.

In brief, the dental kit according to the present invention, comprises spaced support rails upon which a plurality of hand held dental instruments are positioned in an openly accessible position. In addition, a plurality of separate compartments are contained within the housing and each compartment is designed to hold a particular type of tooth implement, such as broaches, reamers and spiral fillers in an openly accessible vertical position. Separate compartments are also formed in the housing for holding the medicaments necessary to perform the root canal operation.

In the preferred form of the present invention, a pair of separate fluid reservoirs are also formed within the housing. A sterile fluid, such as alcohol, is contained within one of the reservoirs while an irrigatory fluid is contained within the other fluid reservoir. A hand pump is mounted to the housing for pumping the sterile fluid from its reservoir and to either a working or an accessory well. Both the working and accessory well are removably mounted to the housing so that, upon completion of the root canal operation, the accessory and working well can be removed from the housing, emptied and auto claved. Thereafter, the pump is used to replenish the sterile solution in the working and accessory wells.

The second reservoir containing the irrigatory fluid is further divided into a main chamber and a subchamber. A fluid valve is fluidly connected between the main and subchamber while an irrigatory solvent well is open on one end through the top of the housing and at its other end to the subchamber. Thus, the main chamber can be completely filled with the irrigatory fluid while a relatively small amount of this fluid can be drained into the subchamber via the valve as required for the root canal operation.

The dental kit according to the present invention further comprises an improved means for rapidly and accurately positioning rubber stoppers on reamers. To accomplish this, a wall is positioned within the main well and can be selectively vertically positioned. In addition, a holder secured to the working well supports the reamers so that the reamers extend downwardly into the interior of the well and abut against the movable wall. Thus, after the movable wall is adjusted to the desired spacing between the holder and the movable wall, the proper position of the rubber stoppers on the reamers can be easily and rapidly visually determined since the rubber stoppers, when properly positioned, should abut against the holder.

A primary advantage of the dental kit according to the present invention is that it contains all of the instruments, implements and medicines necessary to perform a root canal operation. The kit is, furthermore, compact in construction and can be easily transported from office to office. Thus, the kit functions not only as a storage tray but also as a delivery tray. Moreover, the various instruments and implements are segregated from each other in an organized fashion so that the proper instruments, implements or medicaments can be rapidly located and removed during the course of the root canal operation.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
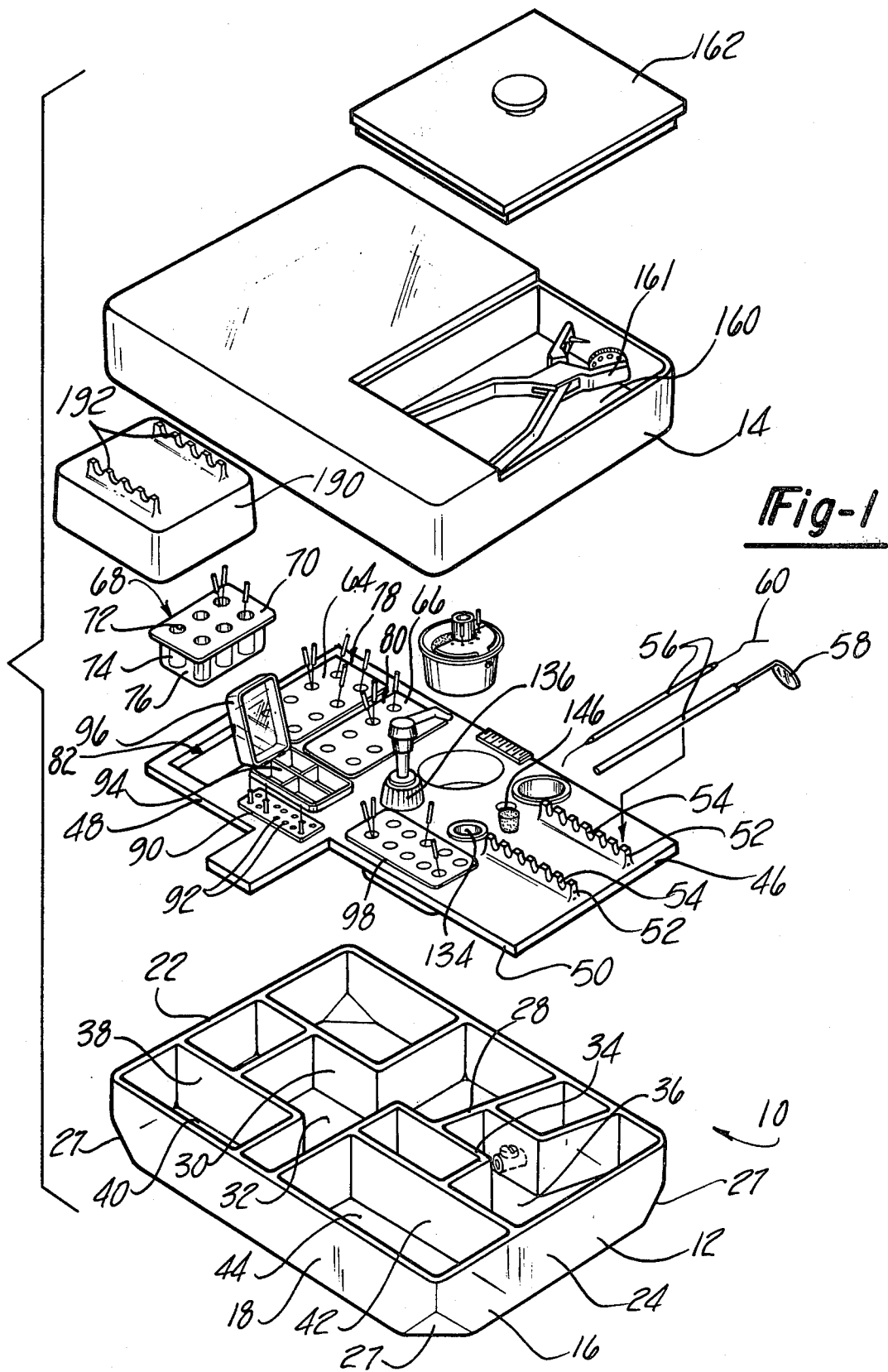
FIG. 1 is an exploded perspective view of a preferred embodiment of the dental kit of the present invention.

With reference first to FIG. 1, a preferred embodiment of the dental kit according to the present invention is thereshown and comprises a housing 10 having a base portion 12 and a lid portion 14. The base portion 12 and lid portion 14 of the housing are preferably constructed of plexiglass although other conventional materials, such as stainless steel, can also be used.

Figure 2:
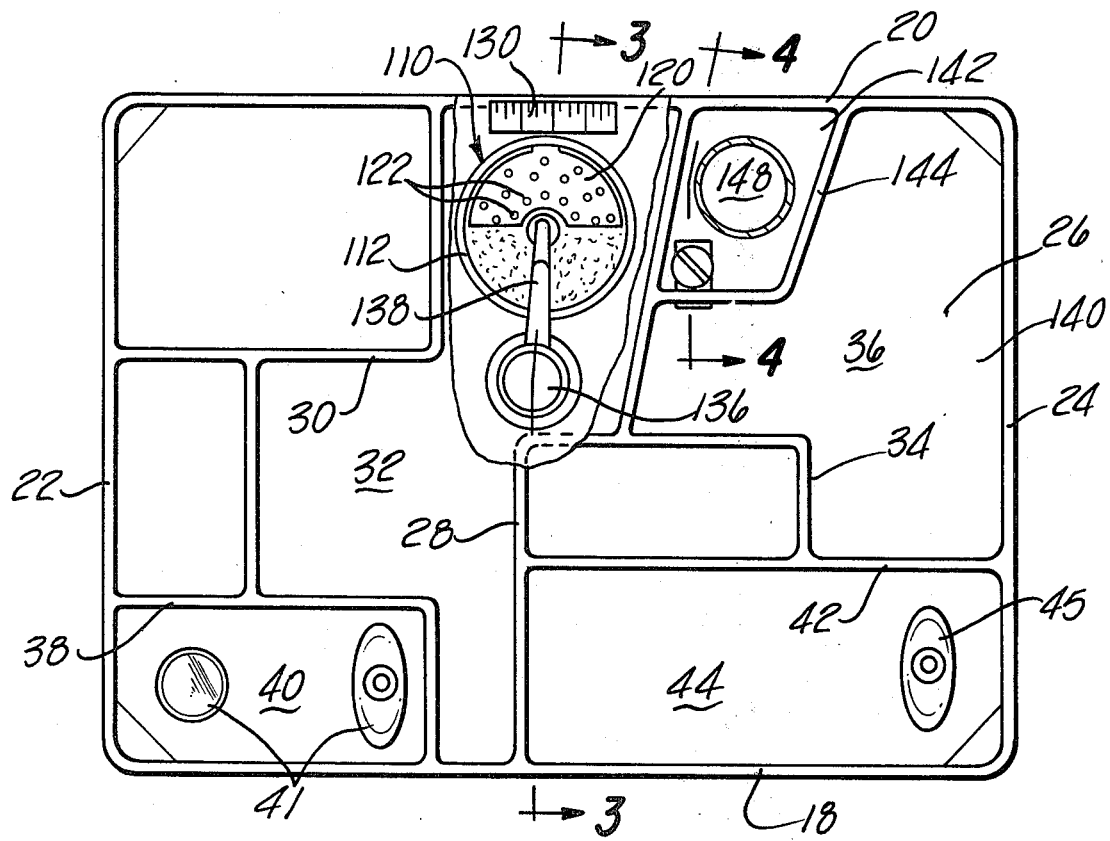
FIG. 2 is a plan view of a part of the dental kit and with parts removed for clarity.

Referring now particularly to FIGS. 1 and 2, the base portion 12 of the housing 10 further comprises a bottom wall 16, a front wall 18, rear wall 20 and side walls 22 and 24. The front wall 18, rear wall 20 and side walls 22 and 24 are joined together at their intersecting corners thus defining an interior housing chamber 26.

The corners of the base portion 12 are bevelled as shown at 27 so that the base portion 12 can fit into a standard front or rear delivery system.

A first dividing wall 28 extends between the front wall 18 and rear wall 20 of the housing base portion 12 which cooperates with a second dividing wall 30 also effectively extending between the front wall 18 and rear wall 20 to form a first fluid reservoir 32 within the housing base portion 12. Similarly, a third dividing wall 34 intersects the first dividing wall 28 along a mid-portion and extends to one side wall 4 to form a second fluid reservoir 36. A first compartment wall 38 also extends between one side wall 22 of the housing base portion 12 and intersects the second dividing wall 30 to form a compartment 40 adjacent the corner of the intersection of the front wall 18 with the side wall 22. Similarly, a second compartment side wall 43 extends between a mid-point of the first dividing wall 28 and the side wall 24 to form a second compartment 44 adjacent the intersection of the side wall 24 with the front wall 18. Moreover, the dividing walls 28, 30 and 34 and also the compartment walls 38 and 42 are fluidly sealed together at their respective intersections with each other and with the housing walls.

Referring now particularly to FIG. 1, the housing base portion 12 comprises a planar cover 46 which is positioned over the top of the side walls 22 and 24, front wall 18 and rear wall 20. The cover 46 includes a pair of cut outs 48 and 50 which register with the compartments 40 and 44 so that the compartments 40 and 44 are open to the bottom wall 16 of the base portion 12. The cover 46, however, does cover both of the fluid reservoirs 32 and 36.

A pair of elongated spaced parallel rails 52 are secured to the cover 46 adjacent one side wall 24 of the base portion 12. The rails 52 have a plurality of aligned notches 54 formed on their top which are adapted to hold a plurality of hand held dental instruments 56 (only two of which are shown) in an openly accessible position. The dental instruments 56 form the necessary hand held dental intruments for performing root canal therapy and comprise, for example, a dental mirror 58 and a plugger 60, explorer and cotton pliers (not shown).

Still referring to FIG. 1, a plurality of holder assemblies 64, 66 and 68 are mounted to the housing base portion 12 adjacent the intersection of the rear wall 20 with the side wall 22. Each of the holder assemblies 64, 66 and 68 are similar in construction and comprise an upper flat plate 70 having a plurality of apertures 72 formed through it. One end of a tube 74 is aligned with each aperture 72 while the other end of each tube 74 is closed by a bottom plte 76. The holder assemblies 64, 66 and 68 are positioned through respective receiving openings 78, 80 and 82 formed through the base portion cover 46 and each of these openings 78–82 are smaller in cross-sectional area than the top plate 70. Thus, the top plate 70 of each holder assembly 64–68 rest upon the cover 46. Moreover, each of the openings 78–82 are formed through the cover 46 between the second dividing 30 and the side wall 22 so that the holder assemblies 64, 66 and 68 are positioned outside of the reservoir 32.

Each of the holder assemblies 64, 66, 68 and 98 (subsequently described in greater detail) are designed to hold a particular type of tooth working implement in an openly accessible vertical position. For example, files normally used during root canal therapy can be positioned within the holder assembly 64 while broaches can positioned within the holding assembly 66. Likewise, adsorbant points can be positioned within the final holding assembly 68. Moreover, since each holding assembly includes a plurality of tubes 74 in which the various tooth working implements are contained, each tooth working implement can be organized within its particular holding assembly by size or type.

A special holder assembly 90 is also secured to the cover 46 adjacent the first compartment 40 for holding spiral fillers often times used with root canal therapy. The holder 90 has a plurality of spaced recesses 92 drilled or otherwise formed in it which correspond to the size of the shank for a spiral filler. Thus, each spiral filler is individually inserted into one cavity 92 of the holder assembly 90 and maintained in an openly accessible position. The cavities 92, however, do not extend entirely through the holder assembly 90 so that the holder assembly 90 can be positioned above the first reservoir 32 and still be maintained separately from it.

A case 94 for holding rubber stops, commonly positioned over broaches and files during root canal therapy, is also secured to the cover 46 adjacent the holder assembly 90. This case is divided into four compartments and can contain not only stoppers but also root canal rain sponges and sterile cotton pellets. The case 94 includes a pivotal cover 96 to prevent the rubber stops and other said items from becoming lost.

Still referring to FIG. 1, a further holder assembly 98 is mounted to the cover 46 adjacent the second compartment 44. The holder assembly 98 is similar in construction to the holder assemblies 64–68 and, as such, will not be further described. The holder assembly 98 is designed to hold gutta percha points and the points can be individually organized with the holder assembly 98 by type and/or size. The holder assembly maintains the gutta percha points in an openly accessible vertical position.

Figure 3:
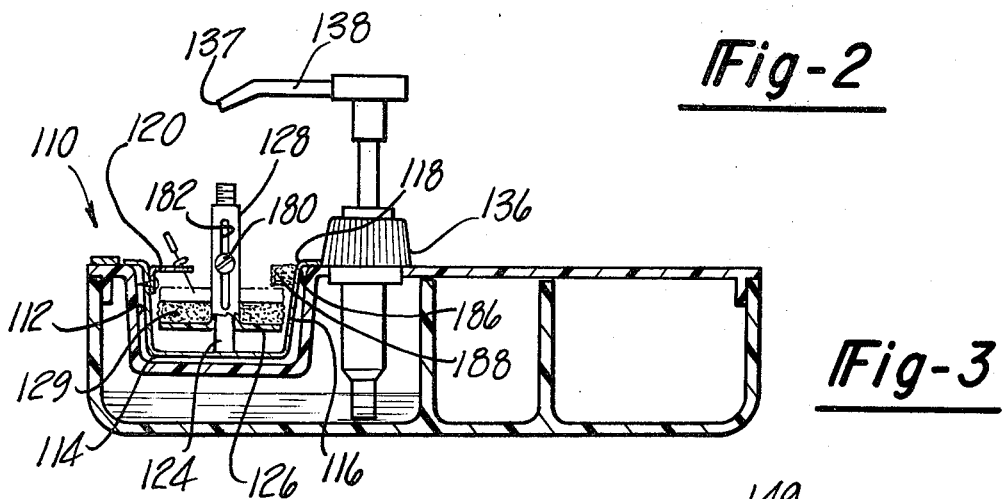
FIG. 3 is a sectional view taken substantially along line 3—3 in FIG. 2.

With reference now to FIGS. 2 and 3, a working and measuring well 110 is positioned within recess 12 in the housing cover 46. The working well 110 includes a bottom wall 114 and a closed annular side wall 116 and is open through its top 118. A semicircular plate 120 is secured to the side wall 116 and extends over the top 118 of well 110. A plurality of apertures 122 are formed through the plate 120 so that tooth working implements used in root canal therapy can be inserted through the apertures 122 and downwardly into the interior of the well 110.

Referring now particularly to FIG. 3, a shank 124 is secured to the bottom wall 114 of the well 110 so that the shank 124 extends upwardly toward the top 118 of the well 110. In addition, a circular wall 126 is fixedly secured to or formed as a part of a tubular member 128 which is slidably positioned over the shank 124 so that the vertical position of the circular wall 126 can be varied. Axial movement of the wall 126 along the shank 124 in turn varies the distance between the wall 126 and the plate 120 mounted to the wall 110 and thus limits the downward extension of the tooth working implements into the well 110.

As shown in FIG. 3, a screw 180 extends through a longitudinal slot 182 in the tubular member 128 and threadably engages the shank 124. Thus, the axial position of the tubular member 128 and also of the movable wall 126 can be locked in any adjusted position by merely tightening the screw 182. In addition, an indicia scale 184 can be provided on the shank 124 to indicate the actual position of the movable wall 126.

The construction of the working well 110 is thus advantageous in that a rubber stopper from the case 94 can be placed on a tooth working implement, such as a reamer, for a distance equal to the depth of the root canal as is the conventional practice. A linear measuring scale 130 (FIG. 2) is mounted to the housing cover 46 to facilitate this. Then, once the rubber stopper has been properly positioned on the reamer, the reamer is positioned through one of the apertures 122 in the plate 120 so that the tip of the reamer extends downwardly into the well 110. Thereafter, the tubular member 128, with its attached movable wall 126 is rotated until the lower end of the reamer abuts against the movable wall 126. Thereafter, rubber stoppers can be positioned on the tooth working implements without measurement and inserted through the holder apertures 122 and into the working well 110. Then if the rubber stopper is held above the plate 120 as the lower end of the implement abuts against the movable plate 126, the dentist merely shifts the rubber stopper downwardly until it abuts against the plate 120 at which time the proper position of the rubber stopper is obtained. Conversely, if the rubber stopper is initially positioned too close its free end, the tooth working implement will tilt to one side thus indicating to the dentist that the rubber stopper must be moved upwardly on the implement. However, since this measurement is not critical, an auto clavable sponge material 129 preferably covers the movable wall to prevent damage to the reamer tips.

The well 110 also preferably includes a brush 186 which is removably mounted to a pin 188 on the well 110. The brush is used to remove root debris from the reamers and the like and is discarded after each operation.

Referring now to FIGS. 1-3, an accessory working well 134 in the form of a receptacle is also positioned within an opening in the base portion cover 46. Both the working well 110 and the accessory well 134 must be at least partially filled with a sterile fluid, such as alcohol and, for this purpose the reservoir 32 is filled with alcohol or a sterlizing solution. A manually operated pump 136 is mounted to the cover 46 and is open at its lower end to the first reservoir 32. Manual depression of the pump 136 pumps fluid from the reservoir 32 and out through the distal end 137 of a spout 138. The spout 138 is rotatable so that the pump 36 can be used to pump alcohol from the reservoir 32 and into either the main working well 110 or the accessory working well 134.

Figure 4:
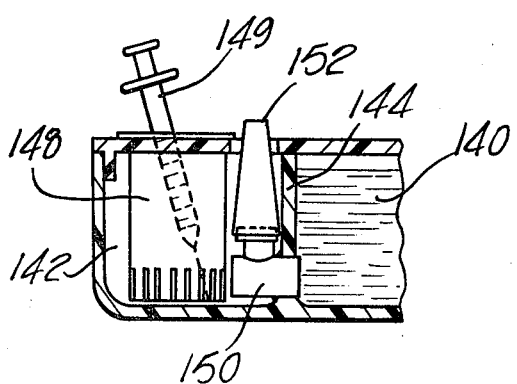
FIG. 4 is a fragmentary sectional view taken substantially along line 4—4 in FIG. 2.

Referring now particularly to FIGS. 2 and 4, the second fluid reservoir 36 is divided into a main chamber 140 and a subchamber 142 by a dividing wall 144. The second fluid reservoir 36 is filled with an irrigatory fluid, preferably through a filler hole 146 (FIG. 1), which is used during root canal therapy. An irrigatory solvent well 148 is open through the cover 46 and, at its lower end, is open to the subchamber 142.

A valve 150 having a valve actuator 152 accessible from the top of the cover 46 is used to selectively provide fluid communications between the main chamber 140 and the subchamber 142 of the reservoir 36. Thus, the main chamber 140 can be completely filled with an irrigatory solvent and, at the start of the root canal operation, the valve 150 is opened thus draining a portion of the irrigatory fluid from the main chamber 140 and to the subchamber 142. This irrigatory fluid is removed by a syringe 149 and used during the root canal therapy and subsequently discarded. At the start of a subsequent root canal operation, the valve 150 is again temporarily opened thus draining another portion of the irrigatory solvent from the main chamber 140 and to the subchamber 142 and thereafter the valve 150 is closed. Since the main chamber 140 is considerably greater in volume than the subchamber 142, a plurality of root canal operations can be performed before the irrigatory fluid in the reservoir 36 must be replenished.

With reference to FIGS. 1 and 2, the housing compartment 44 is designed to contain the various medicaments 45 is standardized squeeze drop plastic bottles utilized during a root canal operation. Further, the compartment 44 can house preformed posts, threaded pins and scissors. Similarly, the compartment 40 is used to contain glass mixing slab and root canal sealer 41 in standardized snap top and squeeze drop plastic bottles.

With reference now particularly to FIG. 1, the lid portion 14 of the housing preferably contains a compartment 160 in which rubber dam tools 161 (only one illustrated) are contained. An auxiliary lid 162 removably closes the compartment 160.

If desired, a lid 190 (FIG. 1) can be provided which fits over the holder assemblies 64 and 66. The lid 190 not only maintains the sterility of the holder assemblies 64 and 66 but also has support rails 192 for holding additional hand held instruments.

The entire kit is constructed of autoclavable plastic and stainless steel components. Alternatively, the individual storage units such as the working well 110 and the like, can be individually removed for autoclavable.

From the foregoing, it can be seen that the dental kit according to the present invention contains all of the tools, implements and supplies necessary to perform root canal therapy. Moreover, the tools, implements and supplies are contained within the kit in an organized fashion which enhances the efficiency of the overall root canal operation without any sacrafice, whatsoever, to the quality and effectiveness of the root canal therapy. Moreover, the implements, instruments and supplies are maintained in an openly accessible position and are vertically accessible from the housing.

The dental kit according to the present invention is further advantageous in that it provides an improved working well with means to accurately and rapidly determine the correct position of rubber stoppers on the reamers and other tooth working implements to prevent damage to the periodontal tissues.

A still further advantage of the dental kit of the present invention is that the dental kit can be easily transported from one office and to the next thus eliminating the necessity of separate endodontic supplies for separate offices.

Having described my invention, however, many modifications thereto will become apparent to those skilled in the art to which it pertains without deviation from the spirit of the invention as defined by the scope of the appended claims.

I claim:

1. A dental device for containing tools, medicines and supplies for performing root canal therapy comprising:
a housing having a base and a lid, said lid dimensioned to fit over and cover said base,
a plurality of holder assemblies, each holder assembly comprising a body having a plurality of receiving openings formed in it, said receiving openings in each holder assembly being dimensioned to contain a single type of tooth working implement or supply,
said base of said housing including a plurality of openings, each opening dimensioned to receive one holding assembly therein,
said holding assemblies being removably positioned within said openings in said housing base, and wherein said dental device is portable and hand carriable and
wherein said device further comprises a working well removably mounted to said housing base, said working well having a bottom wall and a closed side wall thus defining an interior chamber open at its top, means for supporting at least one tooth working implement adjacent the top of the working well so that the tooth working implement extends downwardly into the interior of the well, a plate contained within the interior of the well and means for variably adjusting the position of the plate with respct to the bottom wall.

2. The invention as defined in claim 1 wherein said housing comprises means for supporting a plurality of hand held dental tools in a openly accessible position.

3. The invention as defined in claim 1 wherein said housing base further comprises a liquid reservoir adapted to contain a sterile liquid, a main working well having means to support at least one tooth working implement, and means to pump liquid from said reservoir and to said main working well.

4. The invention as defined in claim 3 and further comprising an accessory working well on said housing and wherein said pump means is operable to pump liquid to either said main working well or said accessory working well.

5. The invention as defined in claim 1 wherein said housing base further comprises a liquid reservoir adapted to contain and irrigatory liquid, said reservoir further comprising a first chamber, a second chamber and valve means for selectively fluidly connecting said chambers together, and an irrigatory well open at one end exteriorly of said housing base and at its other end to one of said chambers.

6. The invention as defined in claim 1 and further comprising a brush removably mounted to said working well.

7. The invention as defined in claim 1 wherein housing has a bevelled bottom which fits in a standard front or rear delivery system.

8. The invention as defined in claim 1 wherein at least one holder assembly is constructed of an auto clavable material.

9. A dental device for containing tools, medicines and supplies for performing root canal therapy comprising:
a housing having a base and a lid, said lid dimensioned to fit over and cover said base,
a plurality of holder assemblies, each holder assembly comprising a body having a plurality of receiving openings formed in it, said receiving openings in each holder assembly being dimensioned to contain a single type of tooth working implement or supply,
said base of said housing including a plurality of openings, each opening dimensioned to receive one holding assembly therein,
said holding assemblies being removably positioned within said openings in said housing base, and wherein said dental device is portable and hand carriable, and
wherein said housing base further comprises a liquid reservoir adapted to contain an irrigatory liquid, said reservoir further comprising a first chamber, a second chamber and valve means for selectively fluidly connecting said chambers together, and an irrigatory well open at one end exteriorly of said housing base and at its other end to one of said chambers.

* * * * *

UNITED STATES PATENT AND TRADEMARK OFFICE
CERTIFICATE OF CORRECTION

PATENT NO. : 4,353,694
DATED : October 12, 1982
INVENTOR(S) : Joseph J. Pelerin

It is certified that error appears in the above—identified patent and that said Letters Patent is hereby corrected as shown below:

Column 3, line 29, after "24. The" insert --bottom wall 16, the--.

Column 3, line 42, delete "4" and insert --24--.

Column 4, line 15, delete "plte" and insert --plate--.

Column 4, line 31, after "can", insert --be--.

Column 4, line 55, delete "rain" and insert --drain--.

Column 6, line 9, delete "36" and insert --136--.

Column 6, line 41, delete "is" and insert --in--.

Column 6, line 60, delete "autoclavable" and insert --autoclaving--.

Column 6, line 67, delete "sacrafice" and insert --sacrifice--.

Column 7, line 48, delete "respct" and insert --respect--.
Column 8, line 14, delete "and" and insert -- an --.

Signed and Sealed this

Eighth Day of February 1983

[SEAL]

Attest:

GERALD J. MOSSINGHOFF

Attesting Officer     Commissioner of Patents and Trademarks